United States Patent
Martis et al.

(10) Patent No.: US 6,380,163 B1
(45) Date of Patent: Apr. 30, 2002

(54) PERITONEAL DIALYSIS SOLUTIONS WITH POLYPEPTIDES

(75) Inventors: Leo Martis, Long Grove; Ron Burke, Arlington Heights, both of IL (US); Dirk Faict, Assenede (BE)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 07/995,106

(22) Filed: Dec. 22, 1992

(51) Int. Cl.$^7$ .............................................. A61K 38/08
(52) U.S. Cl. ........................... 514/16; 514/14; 514/15; 514/2; 514/17; 514/18; 514/19; 514/23
(58) Field of Search ................................ 514/2, 12–19, 514/23; 424/400

(56) References Cited

U.S. PATENT DOCUMENTS

| | | | | |
|---|---|---|---|---|
| 3,939,261 A | * | 2/1976 | Barth | 424/49 |
| 4,179,338 A | | 12/1979 | Gordon | 435/243 |
| 4,309,417 A | | 1/1982 | Staples | 424/128 |
| 4,361,587 A | | 11/1982 | Brule et al. | 426/42 |
| 4,448,716 A | * | 5/1984 | Tsau | 260/112.5 |
| 4,604,379 A | | 8/1986 | Twardowski et al. | 514/21 |
| 4,614,657 A | * | 9/1986 | Sheng | 426/96 |
| 4,631,211 A | * | 12/1986 | Houghton | 428/35 |
| 4,761,237 A | | 8/1988 | Alexander et al. | 210/647 |
| 4,886,789 A | | 12/1989 | Milner | 514/60 |
| 4,906,616 A | | 3/1990 | Gilchrist et al. | 514/21 |
| 4,959,175 A | * | 9/1990 | Yatzidis | 252/364 |
| 5,010,175 A | * | 4/1991 | Rutter | 530/334 |
| 5,011,826 A | * | 4/1991 | Steudle | 514/23 |
| 5,039,609 A | * | 8/1991 | Klein | 435/68.1 |
| 5,053,393 A | * | 10/1991 | Tjoeng | 514/18 |
| 5,100,875 A | * | 3/1992 | De Rotrou | 514/18 |
| 5,182,366 A | * | 1/1993 | Heubner | 530/334 |
| 5,192,746 A | * | 3/1993 | Lobl | 514/11 |
| 5,211,643 A | | 5/1993 | Reinhardt et al. | 604/416 |

FOREIGN PATENT DOCUMENTS

| | | | |
|---|---|---|---|
| EP | 0076355 | 4/1983 | A61M/1/03 |
| EP | 0153164 | 8/1985 | A61M/1/28 |
| EP | 0170275 | 6/1986 | A61K/31/72 |
| EP | 0270545 | 9/1990 | A61K/37/18 |
| EP | 0218900 | 1/1992 | A61K/37/18 |
| WO | 8703786 | 7/1987 | A23J/3/00 |

OTHER PUBLICATIONS

The Merck Index, item 4353 (11th ed., Merck & Co. 1989).*
Van Molde, *Physical Biochemistry*(Prentice Hall), 1971, pp. 26–30 and pp 38–47.*

* cited by examiner

*Primary Examiner*—Christopher S. F. Low
*Assistant Examiner*—David Lukton
(74) *Attorney, Agent, or Firm*—Paula Kelly; Robert M. Barrett (57) ABSTRACT

The present invention provides an improved dialysis solution. The improved dialysis solution provides for the use of specific polypeptides as an osmotic agent with an additional osmotic agent such as dextrose. To this end, the present invention provides, in an embodiment, a peritoneal dialysis solution comprising as osmotic agents approximately 0.25 to about 4.0% (w/v) polypeptides and approximately 0.5% to about 4.0% (w/v) dextrose. The polypeptides have well defined characteristics.

34 Claims, 5 Drawing Sheets

PERITONEAL DIALYSIS SOLUTIONS WITH POLYPEPTIDES

BACKGROUND OF THE INVENTION

The present invention relates generally to peritoneal dialysis. More specifically, the present invention relates to improved peritoneal dialysis solutions including polypeptides.

It is known to use dialysis to support a patient whose renal function has decreased to the point where the kidneys no longer sufficiently function. Two principal dialysis methods are utilized: hemodialysis; and peritoneal dialysis.

In hemodialysis, the patient's blood is passed through an artificial kidney dialysis machine. A membrane in the machine acts as an artificial kidney for cleansing the blood. Because it is an extracorporeal treatment that requires special machinery, there are certain inherent disadvantages with hemodialysis.

To overcome the disadvantages associated with hemodialysis, peritoneal dialysis was developed. Peritoneal dialysis utilizes the patient's own peritoneum as a semipermeable membrane. The peritoneum is a membranous lining of the; body cavity that due to the large number. of blood vessels and capillaries is capable of acting as a natural semipermeable membrane.

In peritoneal dialysis, a dialysis solution is introduced into the peritoneal cavity utilizing a catheter. After a sufficient period of time, an exchange of solutes between the dialysate and the blood is achieved. Fluid removal is achieved by providing a suitable osmotic gradient from the blood to the dialysate to permit water outflow from the blood. This allows the proper acid-base, electrolyte and fluid balance to be returned to the blood. and the dialysis solution is simply drained from the body cavity through the catheter.

Although there are many advantages to peritoneal dialysis, one of the difficulties that has been encountered is providing a dialysate that includes a suitable osmotic agent. What is required is that a sufficient osmotic gradient is achieved. The osmotic agent is used in the dialysis solution to maintain the osmotic gradient required to cause transport of water and toxic substances across the peritoneum into the dialysis solution.

The appropriate osmotic agent needs to achieve at least a couple criteria. First, it needs to be non-toxic and substantially biologically inert. However, the agent should be metabolizable. Additionally, the agent should not rapidly cross the peritoneal membrane into the blood. By achieving both these criteria, this would allow maintenance of the maximum ultrafiltration gradient, and also would prevent toxicity or accumulation of unwanted substances in the blood.

No currently used substance completely satisfies the criteria for an osmotic agent in a dialysis solution. Presently, the osmotic agent that is most widely used is dextrose. Dextrose is fairly safe and is readily metabolized if it enters the blood. However, one of the problems with dextrose is that it is readily taken up by the blood from the dialysate. Because dextrose crosses the peritoneum so rapidly, the osmotic gradient is dissipated within two to three hours of infusion. This can cause reversal of the direction of ultrafiltration, causing water to be reabsorbed from the dialysate toward the end of the time allowed for the exchange.

Another concern with respect to dextrose is that because it is taken up so rapidly by the blood, it can represent a large proportion of the patient's energy intake. While this may not significantly effect a non-diabetic patient, it can represent a severe metabolic burden to a patient whose glucose tolerance is already impaired. Dextrose can also cause problems with respect to hyperglycemia and obesity.

Still further, a problem with dextrose is with respect 'to the preparation of a dialysis solution. Typically, dialysis solutions, similar to other medical products, are sterilized by heating. Unfortunately, heat sterilization of dextrose at physiological pH's will cause dextrose to caramelize. To compensate for this problem, it is known to adjust the pH of the dialysate to within the range of 5 to 5.5; at this low pH dextrose will not caramelize when heated. However, it is believed that this low pH may be responsible for the pain experienced by some patients on in flow of dialysis solution and may cause other problems, e.g., may effect peritoneal host defense.

To address some of the above concerns, a number of substances have been proposed as alternatives to dextrose. However, none of the proposed materials has proven to be an adequate substitute for dextrose.

For example, dextrans, polyanions, and glucose polymers have been suggested as replacements for dextrose. Because of their high molecular weight, it is believed that their diffusion across the peritoneum and into the blood should be minimized. But, the low osmotic activity per unit mass of these materials dictates the need for larger concentrations (w/v) of these materials in the dialysis fluids in order for them to be effective. Additionally, systemic absorption of these concentrations, mainly through the lymphatics, along with slow metabolism, raises serious concern about the long term safety of these agents.

Small molecular weight substances, have also been explored. These substances include glycerol, sorbitol, xylitol, and fructose. However, these. substances are believed to raise a number of safety concerns while offering no substantial advantages over dextrose.

Amino acids appear to be an attractive substitute for dextrose in peritoneal dialysis solution. Short term studies have indicated that they are well tolerated. However, because of their low molecular weights, they are transported quite rapidly through the peritoneum, resulting in rapid loss of the osmotic gradient. In addition, rapid uptake of amino acids leads to a considerable nitrogen burden and limits the use of amino acids to one to two exchanges per day.

Recently, polypeptides have been explored as a potential class of osmotic agents. It is believed that polypeptides will have a slow transport across the peritoneum, and therefore, maintain a prolonged osmotic gradient between dialysate and blood.

U.S. Pat. No. 4,906,616 to Gilchrist et al and European Patent No. 0218900 to Klein set forth polypeptides as the osmotic agent in a peritoneal dialysis, solution. Each of these patents discusses the substitution of. polypeptides for dextrose; polypeptides are the only osmotic agent utilized in the formulations disclosed.

In Gilchrist et al, the bulk of the polypeptides have a molecular weight of 1100 or greater. Indeed, approximately 50% of the peptides have in excess of 18 amino acid residues. The polypeptides are the only osmotic agent used. (see, e.g., col. 4, lines 33–35).

In Klein, the polypeptides are a mixture of relatively low molecular weight, including an alleged substantial portion between 300 to 2,000 daltons, peptides derived from the enzymatic hydrolysis of a high quality protein. The polypeptides are the only osmotic agents used. Further, as long as the mixture of polypeptide falls within an equivalent weight of 150 to 1,500 and the molecular weight of the polypeptides is between 300 to 2,000 daltons, the polypeptide mixture is sufficient for the needs of Klein.

As set forth in detail in the examples hereinafter in this application, the polypeptide solutions proposed by Klein and Gilchrist et al have very limited clinical utility. Although larger in size, like amino acids, these polypeptide compositions are absorbed from the peritoneum quite rapidly. This leads to uremic symptoms. In addition, these materials contain polypeptides that have the potential of producing allergic reactions. This is due to the size of the polypeptides that are used.

There is therefore a need for an improved peritoneal dialysis solution.

SUMMARY OF THE INVENTION

The present invention provides an improved dialysis solution. The improved dialysis solution provides for the use of specific polypeptides as an osmotic agent with an additional osmotic agent such as dextrose.

To this end, the present invention provides, in an embodiment, a peritoneal dialysis solution comprising as osmotic agents approximately 0.25 to about 4.0% (w/v) polypeptides and approximately 0.5% to about 4.0% (w/v) dextrose.

In an embodiment, the peritoneal dialysis solution includes: approximately 120.00 to about 150.00 (mEq/L) of sodium; approximately 80.0 to about 110.00 (mEq/L) of chloride; 0 to about 45.00 (mEq/L) of lactate; 0 to about 45.00 (mEq/L) of bicarbonate; 0 to about 4.00 (mEq/L) of calcium; and 0 to about 4.00 (mEq/L) of magnesium. Preferably, the pH of the solution is approximately 6.0 to about 7.4.

In an embodiment, the polypeptides are synthetic peptides.

In an embodiment, the present invention provides a peritoneal dialysis solution comprising a polypeptide mixture as an osmotically active agent in an osmotically effective amount. The polypeptide mixture consists of not more than approximately 0.10% of polypeptides having a molecular weight of greater than 1200, not more than approximately 25% of polypeptides having a molecular weight of less than 400, and the weight average of the polypeptide mixture being within the range of approximately 400 to about 900 daltons.

In an embodiment, the peritoneal dialysis solution provides: less than approximately 5 ppm of total heavy metals; and less than approximately 500 ppb aluminum. Additionally, the peptides should have: less than approximately 50 mg/gm sodium; less than approximately 10 mg/gm chloride; less than approximately 0.2 mg/gm potassium; less than approximately 1 mg/gm magnesium; less than approximately 1 mg/gm calcium; less than approximately 1 mg/gm phosphorus; and less than approximately 5 mg/gm lactose.

In an embodiment, a two part peritoneal dialysis solution designed to be mixed prior to infusion into a patient is provided. The two part solution comprises: a first part housed in a first structure including approximately 1.0% to about 8% (w/v) dextrose and a pH of approximately 4.0 to about 5.5; a second part housed in a second structure including approximately 0.5 to about 8.0% (w/v) polypeptides and a pH of approximately 6.0 to about 7.5; and including in either the first or the second structure: 0 to about 300 (mEq/L) sodium; 0.0 to about 250.00 (mEq/L) chloride; 0.0 to about 100.0 (mEq/L) lactate; 0.0 to about 100.0 (mEq/L) bicarbonate; 0.0 to about 10.0 (mEq/L) calcium; and 0.0 to about 10.0 (mEq/L) magnesium.

The present invention also provides for the use of polypeptides that have an amino acid composition that provides a nutritionally effective solution.

In an embodiment, the present invention also provides a solution for delivering drugs to the peritoneum.

An advantage of the present invention is that it provides an improved peritoneal dialysis solution.

Still further, an advantage of the present invention is that it provides an improved osmotic agent for use in a peritoneal dialysis solution.

A further advantage of the present invention is that it provides for the use of synthetic polypeptides for making an improved peritoneal dialysis solution.

Furthermore, an advantage of the present invention is that it provides for the ability to create peritoneal dialysis solutions that are at a physiological pH to help reduce the pain of infusion.

Moreover, an advantage of the present invention is that it has reduced osmolalities along with physiologic pH to restore phagocytic function of macrophages.

Additionally, an advantage of the present invention is that it allows the use of dextrose in the solution and sterilization of same at a pH 4.0 to 5.5 to reduce the degradation products of dextrose.

Still further, an advantage of the present invention is that it provides higher weight average molecular weight of osmotic agents to improve ultrafiltration profile.

Another advantage of the present invention is that it provides balanced supplementation of polypeptides (protein source).and dextrose (energy source) through a dialysis solution to improve the nutritional status of the renal patient.

Moreover, an advantage of the present invention is that it provides for the ability to increase infusion volumes and hence small solute clearances as a result of decrease in molar concentrations of osmotic agents.

Further, an advantage of the present invention is that it provides a solution for intraperitoneal drug delivery.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides improved peritoneal dialysis solutions containing polypeptides having well defined characteristics (e.g., molecular weight distribution, amino acid composition, purity, etc.) for use in peritoneal dialysis solutions and intraperitoneal drug delivery. The polypeptides are preferably used with another osmotic agent such as dextrose, polyglucose, amino acids, and glycerol.

As set forth in detail below, by selecting well defined polypeptides and utilizing same with an additional osmotic agent, the disadvantages of polypeptides alone and dextrose alone can be overcome. To this end, preferably, approximately 0.25% to about 4% (w/v) polypeptides and approximately 0.5% to about 4% (w/v) dextrose are used as the osmotic agent pursuant to the present invention.

In an embodiment, the polypeptides are obtained from enzymatic or acid hydrolysis of high biological value proteins. These proteins can be derived from milk, egg, potato, or soy. The polypeptides are prepared using enzymatic or chemical hydrolysis, dialysis, ultrafiltration, ion exchange, solvent fractionation, chromatography, or other related separation techniques.

For example, whey can be hydrolyzed with a proteolytic enzyme, such as trypsin. The desired molecular weight fraction of the present invention, set forth below, is then separated using ultrafiltration and dialysis. By using ion exchange absorption, ions and heavy metals can be removed. A variety of methods can be used, as known in the art, for preparing such polypeptides.

The polypeptides can, in an embodiment, be synthetic polypeptides. The use of synthetic polypeptides allows one to provide peptides, that have better defined characteristics and contain less impurities as compared with polypeptides that are obtained by hydrolysis proteins.

In order to determine the solutions of the present invention, the Klein solutions were tested. Specifically, immunogenicity and ultrafiltration and absorption were evaluated. Accordingly, the following experiments were performed.

EXAMPLE NO. 1

The purpose of this study was to evaluate peptides, as disclosed in Klein, differing in weight average and number average molecular weights, as alternative osmotic agents to dextrose in dialysate solutions. These experiments were conducted in a nephric unanesthetized rat model.

The following peptide powders were received from E. Klein (University of Louisville).

Run #123 & 132
Run #138
Run #140
Mw=2850,
Mw=2746,
Mw=6647,
Mn=731
Mn=967
Mn=1020

Due to the presence of high levels of endotoxin (>500 EU/ml) in each of the above preparations, a "clean up" procedure was performed as follows: 7% solutions of each peptide preparation was centrifuged to remove black particulate. Each solution was then passed through a 0.2 $\mu$ filter directly into a pre-washed Fresenius F-60 dialyzer to remove endotoxin. The dialyzer was rinsed with sterile water following a single pass of peptide solution. The peptide solutions were transferred into depyrogenated pans and lyophilized. All three peptide preparations were reanalyzed for endotoxin. Results indicated levels below the pyrogenic response level of 0.5 EU/ml.

After removal of endotoxin from the peptides, molecular weight and mean profile changed due to a loss of high molecular weight peptides after passing through the F-60 dialyzer. The final results are shown below:

Run #123 & 132
Run #138
Run #140
Mw=1126,
Mw=1959,
Mw=2364,
Mn=734
Mn=982
Mn=1008

Figure 1:
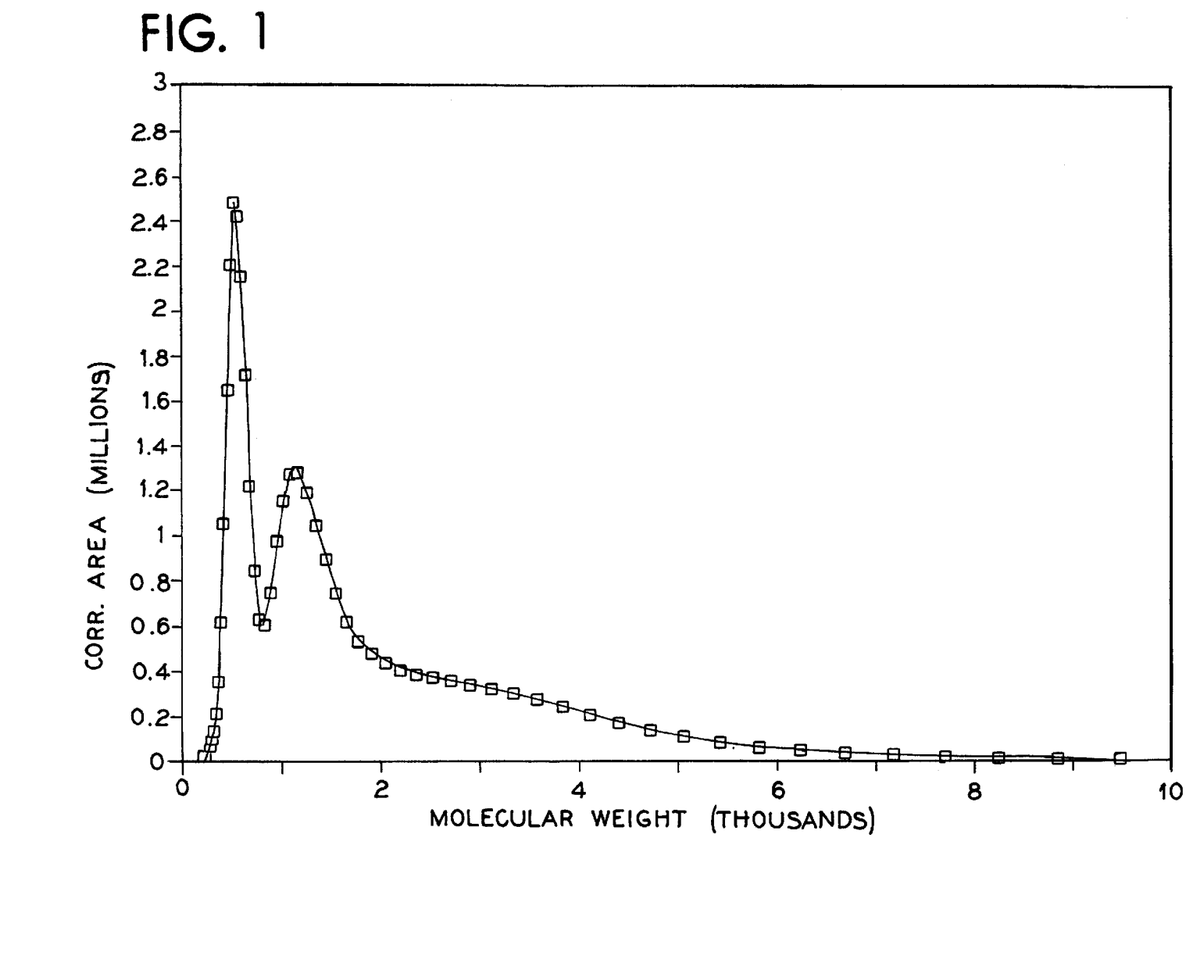
FIGS. 1–3 illustrate, graphically, molecular weight distributions for the peptide mixtures tested in Example No. 1.
Figure 2:
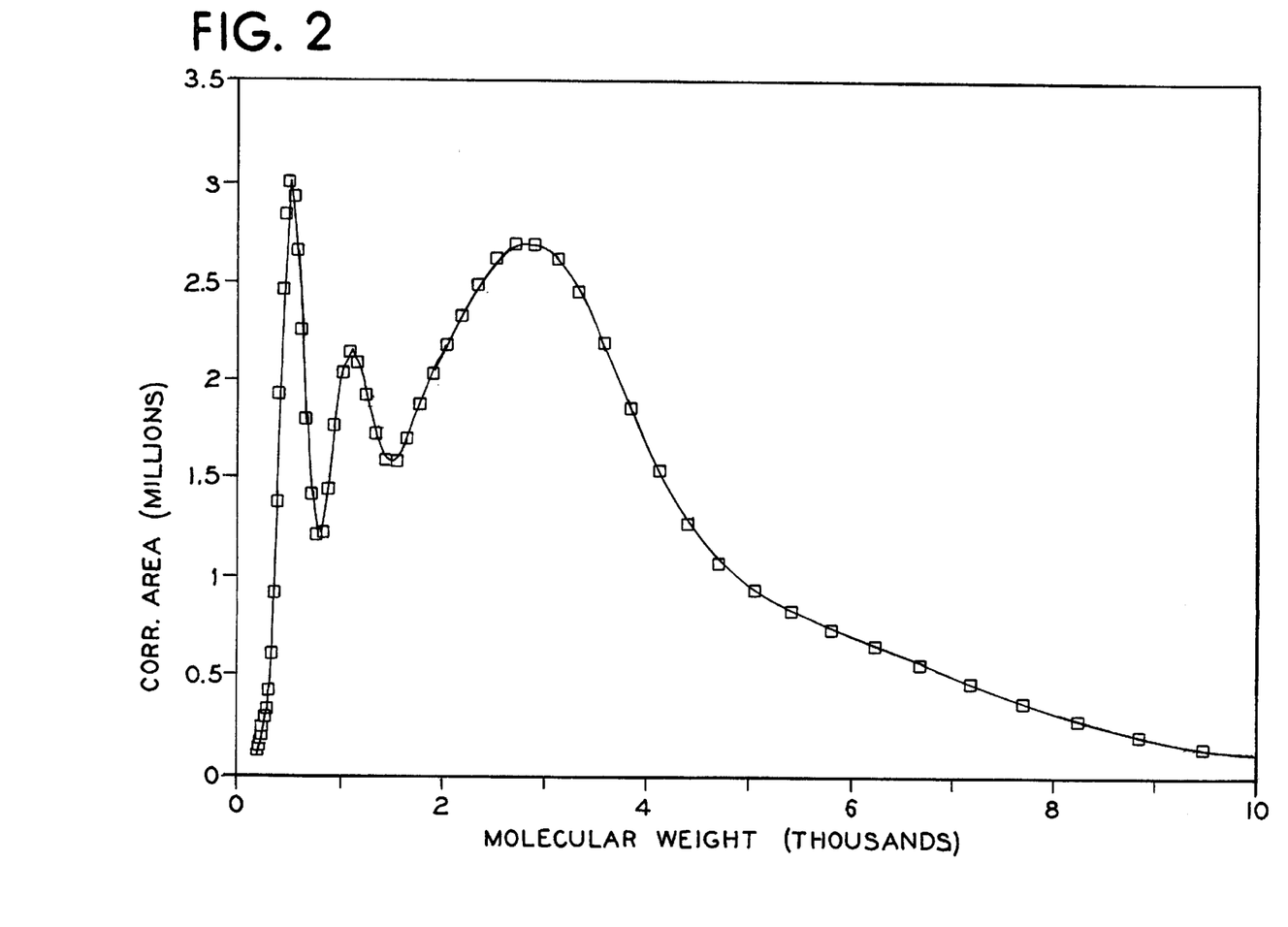
Figure 3:
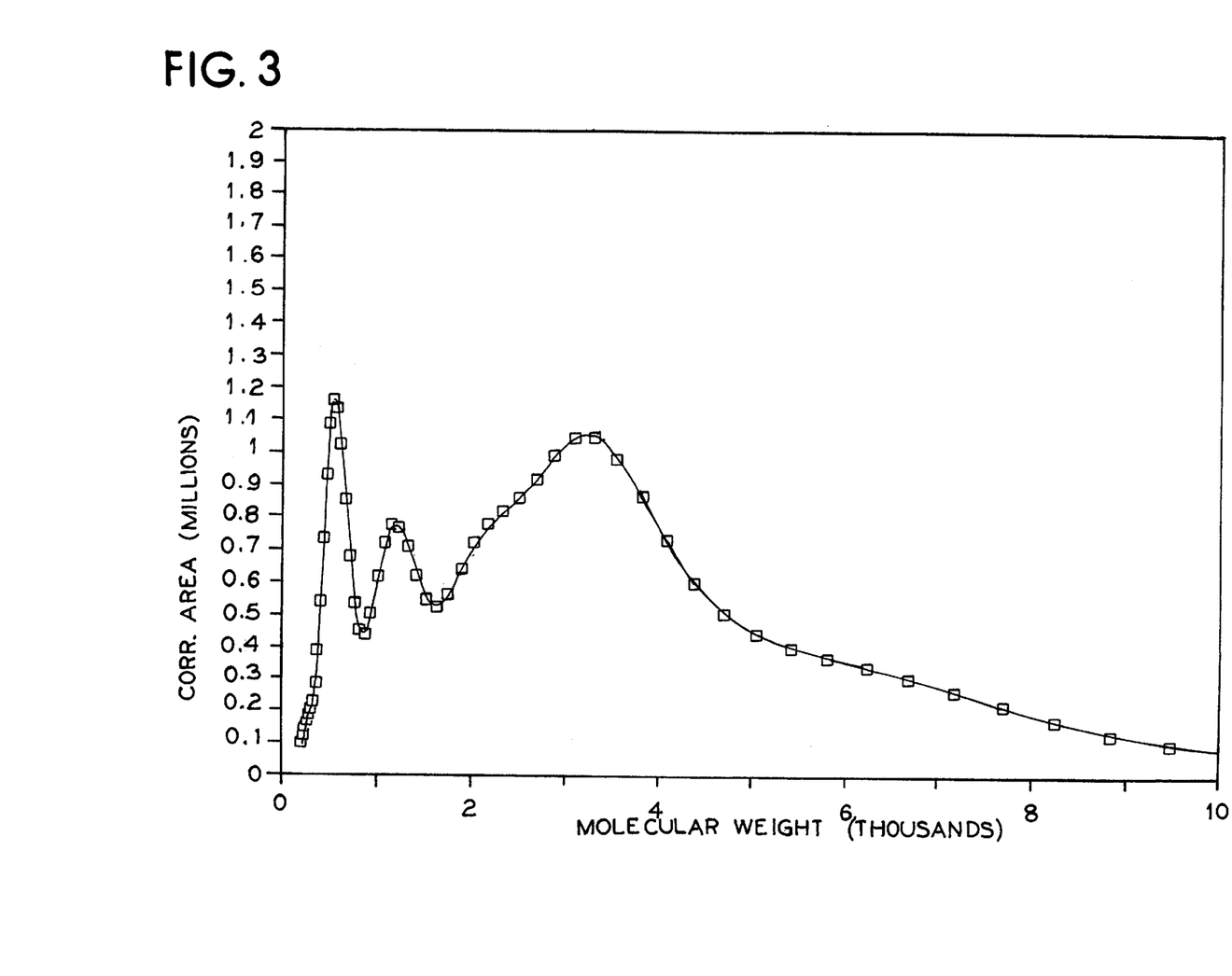

Molecular distributions for each peptide mixture are shown in FIGS. 1–3.

Peptide powders were formulated to match the electrolyte composition of Dianeal® PD-2 as summarized in Table 1.

TABLE 1

Composition of Peritoneal Dialysis Solutions

| Component | 2.5% Dextrose Dianeal ® | Run 132 | Run 138 | Run 140 |
|---|---|---|---|---|
| Peptide (g/dl) | — | 3.5 | 5.5 | 4.3 |
| Dextrose (g/L) | 25 | — | — | — |
| Sodium bound (mEq/L) | — | 25 | 31 | 31 |
| Sodium (mEq/L) | 132 | 148 | 153 | 155 |
| Chloride (mEq/L) | 96 | 86 | 85 | 84 |
| Lactate (mEq/L) | 40 | 40 | 40 | 40 |
| Calcium mg/L | 3.5 | 3.5 | 3.5 | 3.5 |
| Magnesium (mEq/L) | 0.5 | 0.5 | 0.5 | 0.5 |
| Electrolyte total | 272 | 278 | 282 | 283 |
| Osmolality (mOsm/kg) | 383 | 338 | 355 | 335 |
| pH | 5.1 | 7.7 | 7.3 | 7.3 |

Rats were anesthetized by Metafane inhalation. The abdominal area of the rats. was shaved. Dialysate solution (90 ml/kg) was injected intraperitoneally using a 23G needle. The dialysis solution contained approximately 1$\mu$ Ci $^{14}$C Dextran as a dilution marker.

Rats were allowed to recover and permitted free access to water.

Dialysate samples (0.2 ml) were collected at 0.5, 1,2, and 4 hours during the dwell period.

At the end of a 4 hour dwell period, a 1 ml blood sample was collected via the tail artery, plasma separated and frozen. Rats were euthanized by tail vein injection of solution.

The abdominal cavity was opened by midline incision, dialysate collected, and volume recorded.

The experimental procedure was performed as described below.

Rats, n=6 per group were randomly dosed with one of the following dialysate solutions: 1.5% Dextrose DIANEALO®, 2.5% Dextrose DIANEAL®, Peptide run 132, Peptide run 138, or Peptide run 140.

Analyses: $^{14}$C Dextran, all dialysate samples.

Osmolality in all dialysate samples and in all t=4 hr plasma samples.

Amino acids in all dialysate samples containing peptide runs Pre and 4 hr. 0.5 , 1, and 2 hr samples run for some rats in Peptide groups.

Glucose, all Pre and 4 hr dialysate samples in DIANEAL groups.

Figure 4:
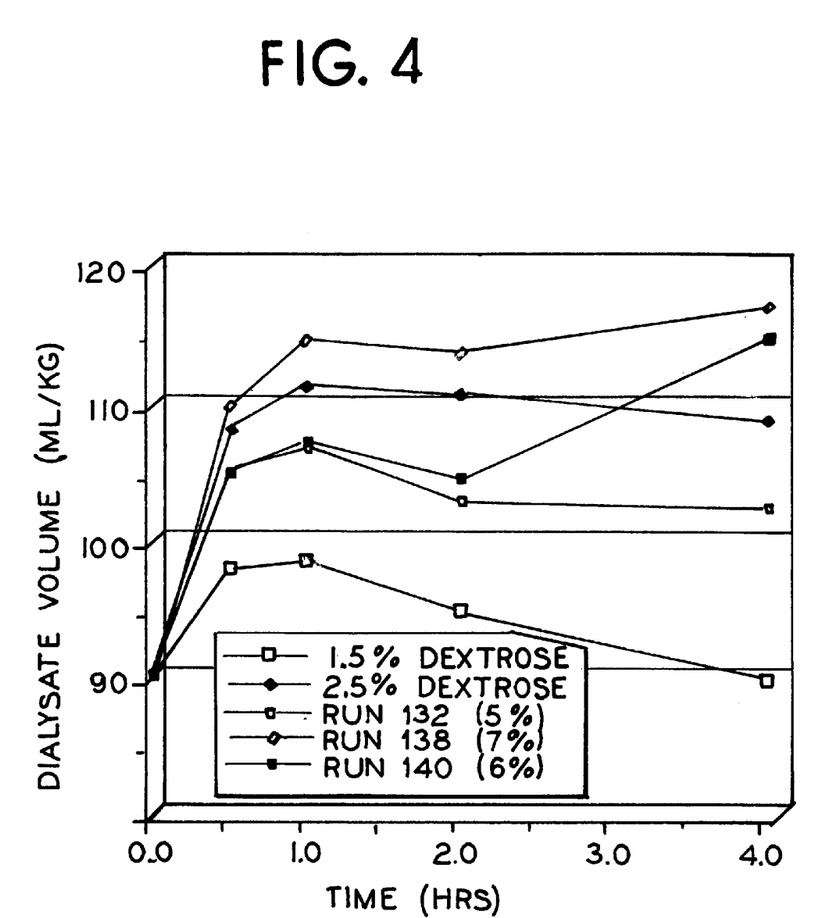
FIG. 4 illustrates, graphically, volume profiles for Example No. 1.

Volume profiles for the experiment are shown in FIG. 4. Volumes between t=0 and the end of the dwell are based on $^{14}$C Dextran concentrations assuming a constant rate for disappearance of $^{14}$C Dextran.

Figure 5:
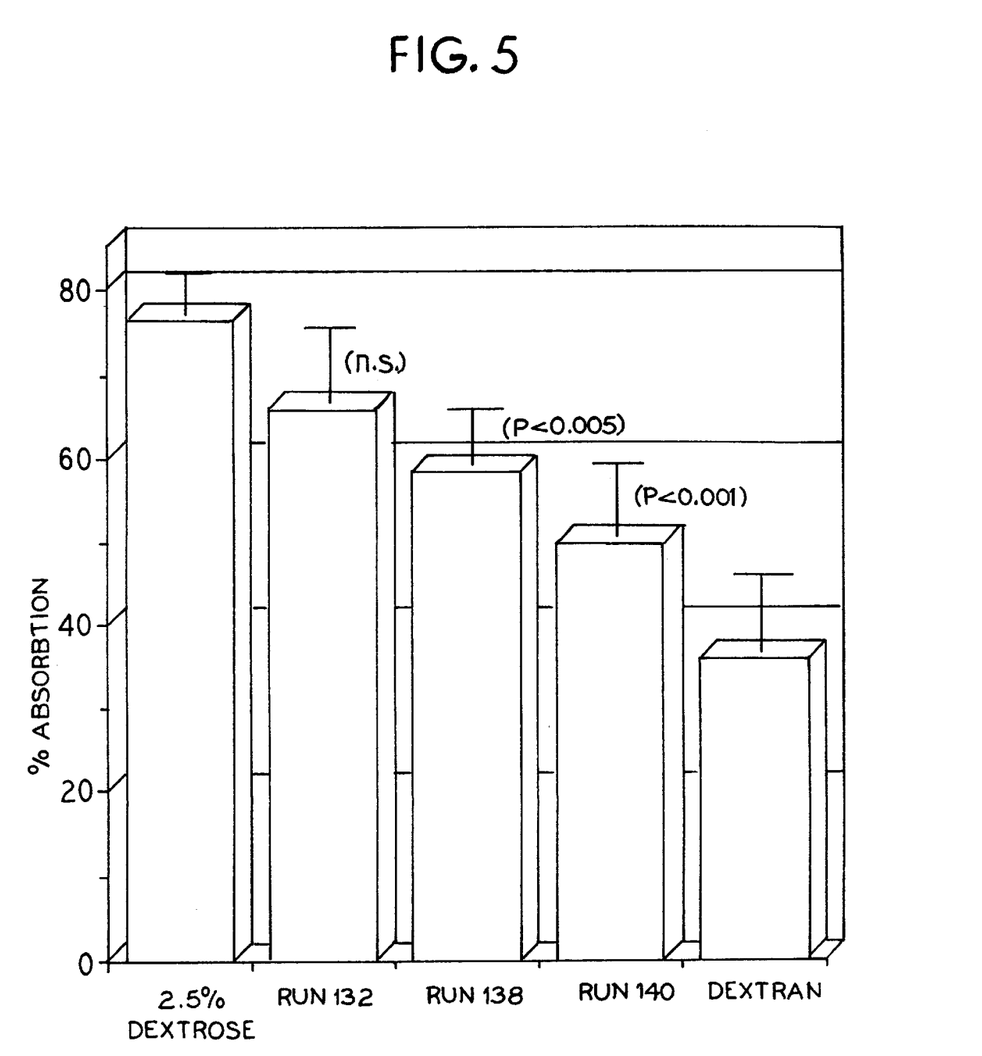
FIG. 5 illustrates, graphically, absorption of dextrose and peptides for Example No. 1.

Dialysate samples were analyzed for amino acids following acid hydrolysis to generate free amino acids. These analyses were used to calculate the percent of peptides absorbed during an exchange as compared to dextrose. The results are shown in FIG. 5.

The experiments demonstrate that a dialysis solution containing peptides can produce ultrafiltration profiles similar to that seen with dextrose but with a lower initial osmolality.

Additionally, the experiments demonstrate that peritoneal absorption of peptides at 4 hours is approximately 50–60%.

EXAMPLE NO. 2

An irritation screening was conducted using 2.5% Dextrose (w/v) in Dianeal®, 1.0% Whey Protein Hydrolysate (in accordance with Klein) (w/v) in 1.5% Dextrose (w/v) in Dianeall, and 3.0% Whey Protein Hydrolysate (in accordance with Klein) (w/v) in 1.5% Dextrose (w/v) in Dianeal®. Two sites were selected and shaved on two animals for each material. Each animal received two 0.105-mL intradermal injections of the respective undiluted material.

A positive control irritation screening was also conducted in the same manner with a 1% w/v concentration of sulfathiazole in sterile 0.9% saline. All sites were scored for erythema and edema at 24 and 48 hours after injection. Since all three test materials were shown to be nonirritating, they were administered undiluted on Day 8 and Day 22 (challenge phase) of the definitive study. The positive control animals received a 5% w/v suspension of sulfathiazole in sterile water for the Day 8 intradermal injections and as a 1% w/v suspension in sterile 0.9% saline for the Day 22 challenge procedure.

The study was conducted using 10 test animals and four naive control animals per test or positive control material. On Day 1, animals in each test group received duplicate 0.05-mL intradermal injections of a 1:1 ratio of Freund's Complete. Adjuvant in sterile water, the respective test material, and a 1:1 ratio of the respective test material in Freund's Complete Adjuvant.

For the positive control group, the animals received duplicate 0.05-mL intradermal injections of a 1:1 ratio of Freund's Complete Adjuvant in sterile water, a 5% w/v suspension of sulfathiazole in sterile water, and a 5% w/v suspension of sulfathiazole in Freund's Complete Adjuvant.

On day 7, animals in all three test groups and the positive control group were pretreated with 10% w/w sodium lauryl sulfate in petrolatum applied topically at the shaved area of the Day 1 intradermal injections. On Day 8, the respective test or positive control material was injected intradermally at a volume of 0.05 mL into two separate areas located just posterior to the initial intradermal injections.

All the test materials were administered undiluted and the, positive control was administered as a 5% w/v suspension of :sulfathiazole in sterile water. All naive control animals were not treated during the induction phase.

Two weeks following the Day 8 intradermal injections, all animals in the respective test and naive control groups received a challenge intradermal injection. The respective undiluted test material was injected intradermally at a volume of 0.05-mL into one site on the shaved right flank of each respective animal. The positive control animals were treated with a 1% w/v suspension of sulfathiazole in sterile 0.9% saline. The sites were examined for erythema and edema at 24, 48, and 72 hours following injection.

No dermal reactions at challenge were observed in the animals treated with 2.5% Dextrose (w/v) in Dianeal®. Dermal sensitization responses were observed in the test animals treated with 1.0% and 2.0%. Whey Protein Hydrolysate (w/v) in 1.5% Dextrose (w/v) -in Dianeal® and in the animals treated with the positive control material. There were no dermal reactions observed in the respective naive control animals.

Based upon the results obtained, the materials are classified as presented below:

| Test Material Identification | Classification |
|---|---|
| 2.5% Dextrose (w/v) in Dianeal ® | Not a sensitizer |
| 1.0% Whey Protein Hydrolysate (w/v) in 1.5% Dextrose (w/v) in Dianeal ® | Sensitizer |
| 3.0% Whey Protein Hydrolysate (w/v) in 1.5% Dextrose (w/v) in Dianeal ® | Sensitizer |
| Sulfathiazole (positive control) | Sensitizer |

| Material Designation | Test Material Identification | Lot Number | Abbreviation | Physical Description |
|---|---|---|---|---|
| Test | 2.5% Dextrose (w/v) in Dianeal ® | C132365 | 25% Dextrose | Clear, colorless liquid |
| Test | 1.0% Whey Protein Hydrolysate (w/v) in 1.5% Dextrose (w/v) in Dianeal ® | P900510 in C127225 | 1.0% WPH | Pale-yellow liquid |
| Test | 3.0% Whey Protein Hydrolysate (w/v) in 1.5% Dextrose (w/v) in Dianeal ® | P900510 in C127225 | 3.0% WPH | Pale-yellow liquid |
| Positive Control | Sulfathiazole | 85F-0409 | — | White powder |

Storage and Retention

The test materials were stored refrigerated. The positive control material was stored at room temperature.

Test Animal

Young adult albino guinea pigs, Hra:(DH)SPF, were procured, maintained individually in screen-bottom stainless steel cages in temperature- and humidity-controlled rooms, provided continuous access to Certified Guinea Pig Chow®5026, Purina Mills, Inc., and water and held for an acclimation period of at least 7 days. If variations from the prescribed environmental conditions existed, they were documented and considered to have no effect on the study outcome. No contaminants were expected to have, been present in the feed or water which would have interfered with or affected the results of the study.

Group Assignments

Sixty-four healthy, acclimated male albino guinea pigs weighing from 354 to 562 g were chosen at random for this study. The animals were individually housed and identified by animal number and corresponding ear tag. The animals were divided into the following groups:

| Group | Number of Animals | Test Material Identification |
|---|---|---|
| 1. Irritation Screening | 2 | 2.5% Dextrose (w/v) in Dianeal ® |
| 2. Irritation Screening | 2 | 1.0% Whey Protein Hydrolysate (w/v) in 1.5% Dextrose (w/v) ln Dianeal ® |
| 3. Irritation Screening | 2 | 3.0% Whey Protein Hydrolysate (w/v) in 1.5% Dextrose (w/v) in Dianeal ® |

-continued

| Group | Number of Animals | Test Material Identification |
|---|---|---|
| 4. Irritation Screening | 2 | Sulfathiazole (Positive Control) |
| 5. Test | 10 | 2.5% Dextrose (w/v) in Dianeal ® |
| 6. Naive Control | 4 | 2.5% Dextrose (w/v) in Dianeal ® |
| 7. Test | 10 | 1.0% Whey Protein Hydrolysate (w/v) in 1.5% Dextrose (w/v) in Dianeal ® |
| 8. Naive Control | 4 | 1.0% Whey Protein Hydrolysate (w/v) in 1.5% Dextrose (w/v) in Dianeal ® |
| 9. Test | 10 | 3.0% Whey Protein Hydrolysate (w/v) in 1.5% Dextrose (w/v) in Dianeal ® |
| 10. Naive Control | 4 | 3.0% Whey Protein Hydrolysate (w/v) in 1.5% Dextrose (w/v) in Dianeal ® |
| 11. Positive Control | 10 | Sulfathiazole |
| 12. Naive Control | 4 | Sulfathiazole |

Test Material Preparation

The test materials, 1.0% WPH and 3.0% WPH, were supplied in sterile glass bottles and were reconstituted with 100-mL of Dianeal® PD-1 with 1.5% Dextrose. Mixing and aliquoting was performed under a hood with static air conditions using aseptic techniques. Using a transfer set, the Dianeals® bag port was spiked, the septum was swabbed with alcohol, and a needle was inserted into the test material vial. The transfer set clamp was opened to allow solution to flow into the vial. The needle was then withdrawn from the vial and the vial was swirled to dissolve the powder into the solution. This procedure constitutes an "undiluted" test material. The 2.5% Dextrose solution was administered as received.

Irritation Screening

The purpose of the irritation screening was to show that each undiluted test material was nonirritating and could be used for the induction and challenge treatments. Two sites were selected and shaved on each of two animals per material. Each animal received two 0.05-mL intradermal injections of the respective undiluted material. A positive control irritation screening was also conducted in the same manner with a 1% w/v concentration of sulfathiazole in sterile 0.9% saline. All sites were scored for erythema and edema at 24 and 48 hours after injection.

Based upon the results obtained from the irritation screening, materials 2.5% Dextrose, 1.0% WPH, and 3.0% WPH were administered undiluted for the Day 8 intradermal injections and the Day 22 challenge, procedure. The positive control animals received a 5% w/v suspension of sulfathiazole in sterile water for the Day 8 intradermal injections and a 1% w/v suspension in sterile 0.9% saline for the Day 22 challenge procedure.

Definitive Study—Induction Phase

Intradermal Injections (Day 1) A 4-cm×6-cm area was clipped along the midline over the shoulder region of each animal in the test and positive control groups. Six intradermal injections were made within the boundaries of a 2-cm×4-cm area, one row of three injections on each side of the midline as follows:

Sites A and B
Groups 5, 7, 9, and 11—0.05 mL of the 1:1 ratio of Freund's Complete Adjuvant in sterile water Sites C and D
Groups 5, 7, and 9—0.05 mL of the respective undiluted test material
Group 11—0.05 mL of the 5% w/v suspension of sulfathiazole in sterile water Sites E and F
Groups 5, 7, and 9—0.05 mL of the respective test material as a 1:1 dilution in Freund's Complete Adjuvant
Group 11—0.05 mL of the 5% w/v suspension of sulfathiazole in a 1:1 Freund's Complete Adjuvant/water solution Sodium Lauryl Sulfate (SLS) Pretreatment (Day 7) One week after the initial intradermal injections, all injection areas of the test group animals and positive control animals were closely shaved and a 10% w/v mixture of SLS in petrolatum was massaged into the skin with a glass rod.

Intradermal Injections (Day 8) The respective test or positive control (5% w/v suspension of sulfathiazole in sterile water) material was injected intradermally at a volume of 0.05 mL into two separate areas located just posterior to the initial intradermal injections.

The naive control animals were not treated during the induction phase of the study.

Challenge Phase

Two weeks after the Day 8 intradermal injections all test and naive control (previously untreated) groups received a challenge injection. All test and naive control groups were treated with the respective undiluted material. The positive control and naive positive control animals received treatment with a 1% w/v suspension and sulfathiazole in sterile 0.9% saline. The hair was removed from a 5.0-cm×5.0 cm area on the right flank by shaving as before. The respective test or positive control material was injected intradermally at a volume of 0.05 mL into one site of the right flank of each respective animal. Approximately 21 hours later, the test sites were closely shaved.

Observations

Twenty-four hours following challenge injection the test sites were examined for erythema and edema. The sites were examined again at 48 and 72 hours after injection to detect any weak, slowly developing reactions. Redness constituted a minimum criterion of allergic reaction. Strongly sensitized animals displayed a vivid redness, associated with indurated swelling. The reactions were scored according to the following scale:

0=No reaction

1=Scattered mild redness

2Moderate and diffuse redness

3=Intense redness and swelling

The animals were observed for clinical signs daily throughout the study. Individual body weights were recorded just prior to initiation of treatment, at weekly intervals throughout the study, and at termination of the experimental phase.

Blood Collection

At experimental termination, all animals from Groups 5, 7, and 9 were anesthetized with carbon dioxide. Approximately 4–5 mL of whole blood was collected via cardiac puncture.

DISCUSSION (Example No. 2)

General Behavior and Appearance

All animals in all groups appeared normal through out the study. There was no significant effect on body weight gain (significant=greater than 10% loss from previously body weight) in any animal throughout the study with the exception of one Group 9 test animal (E17259) treated with 3.0% WPH that exhibited a 52-g loss during the first week on test, another Group 9 animal (E17229) that had a 62-g loss during the second week of the study and one Group 11 positive control animal (E17221) with a 76-g loss during the third week of the study.

CONCLUSION (Example No. 2)

Based on the results obtained, the materials tested are considered to be classified as follows:

| Group | Material | # of Positive Reactions/# in Group | Classification |
|---|---|---|---|
| 5 | 2.5% Dextrose (w/v) in Dianeal ® | 0/10 | Not a sensitizer |
| 7 | 1.0% Whey Protein Hydrolysate (w/v) in 1.5% Dextrose (w/v) in Dianeal ® | 10/10 | Sensitizer |
| 9 | 3.0% Whey Protein Hydrolysate (w/v) in 1.5% Dextrose (w/v) in Dianeal ® | 10/10 | Sensitizer |
| 11 | Positive Control (Sulfathiazole) | 9/10 | Sensitizer |

The above examples (Example Nos. 1 and 2) demonstrated that the use of only a polypeptide mixture such as that set forth in Klein and/or Gilchrist et al is not clinically acceptable in a peritoneal dialysis solution.

In order for the polypeptide composition of Klein to obtain the absorption equivalent to a 2.5% dextrose solution, one needs at least a 5.5% polypeptide solution. However, Example No. 1 demonstrates that the absorption of the polypeptide is at least 50% to 60%. If polypeptides, at an at least 5% concentration in a dialysis solution are used at every exchange, the patient would receive at least 200 grams of amino acids per day. It has been found that peritoneal absorption of more than. 40 grams of amino acids per 24 hours causes uremia in dialysis patients.

Accordingly, due to the absorption characteristics of the polypeptides, it has been determined that preferably only a 1 to 2% concentration of a polypeptide solution, such as Klein, should be used. However, at such a concentration, the polypeptides do not provide a sufficient osmotic agent. It has also been found that in order to control uremia problems, it is necessary to control the proportion of lower molecular weight peptides.

Example No. 2 demonstrates that the polypeptides of Klein have the potential for immunogenicity. The problem stems from the fact that too great a proportion of peptides in Klein have a molecular weight above 1200.

Accordingly, pursuant to the present invention, the polypeptides are used in a concentration of 0.25 to 4 with an osmotic agent, such as dextrose which is used in a concentration of 0.5 to 4 The polypeptides have an average molecular weight of 400 to 900 daltons. It has been found that not more than 0.10% of the polypeptides should have a molecular weight of greater than 1,200. This minimizes the risk of immunogenic response. Additionally, not more than 25% of the polypeptides should have a molecular weight of less than 400. This prevents the uremic problems that will occur with the solution proposed in Klein.

It should be noted that the lower weight peptides are readily absorbed. For a 1% polypeptide solution, if the solution contains more than 25% polypeptides having a molecular weight less than 400, greater than 40 gms amino acid will be absorbed by the patient causing uremia. Accordingly, the polypeptides, pursuant to the present invention, are limited to less than or equal to 25% having a molecular weight less than 400.

Polypeptides can be used alone or in combination with amino acids as nutritional supplements in a dialysis solution to correct protein malnutrition.

Preferably, in an embodiment, the polypeptides used in the present invention include the following amino acid profile.

| Amino Acid Composition | |
|---|---|
| ASX | 10.3 |
| GLX | 20.3 |
| SER | 4.5 |
| GLY | 2.3 |
| HIS | 2.4 |
| ARG | 2.3 |
| THR | 5.7 |
| ALA | 6.4 |
| PRO | 5.8 |
| TYR | 3.7 |
| VAL | 4.6 |
| MET | 2.3 |
| ILE | 4.7 |
| LEU | 11.7 |
| PHE | 3.4 |
| LYS | 9.7 |

To this mixture 50 to 150 mg valine and 15 to 30 mg tryptophan are added per gm of peptides. This composition provides improved nutritional benefits to the patient.

To provide a balanced nutritional solution, preferably, the ratio of polypeptides to dextrose, in the solution is 0.3 to 2 by weight.

By way of example, and not limitation, the dialysis solution should comprise, in addition to the polypeptides

| Total heavy metals | <5 ppm |
|---|---|
| Aluminum | <500 ppb |
| With respect to peptides used, they should comprise: | |
| Sodium | <50 mg/gm |
| Chloride | <10 mg/gm |
| Potassium | <0.2 mg/gm |
| Magnesium | <1 mg/gm |
| Calcium | <1 mg/gm |
| Phosphorus | <1 mg/gm |
| Lactose | <5 mg/gm |

The polypeptides dialysis solution can be formulated in a single bag or in two separate containers. In an embodiment, the polypeptides can be formulated in a single bag with glycerol as an additional osmotic agent.

In an embodiment, the present invention provides a peritoneal dialysis solution that is housed in two separate units and then mixed prior to use. These units can be two separate containers or they can be two chambers of a single bag.

By way of example, and not limitation, the composition contained in separate chambers can be as follows:

| | Chamber 1 | Chamber 2 |
|---|---|---|
| Dextrose (% w/v) | 1.0–8.0 | |
| Polypeptides (% w/v) | 0.0 | 0.5–8.0 |
| Sodium (mEq/L) | 0–300 | 0–300 |
| Chloride (mEq/L) | 0–250 | 0–250 |
| Lactate (mEq/L) | 0–100 | 0–100 |

-continued

|  | Chamber 1 | Chamber 2 |
|---|---|---|
| Bicarbonate (mEq/L) | 0–100 | 0–100 |
| Calcium (mEq/L) | 0–10 | 0–10 |
| Magnesium (mEq/L) | 0–5.0 | 0–5.0 |
| pH | 4.0–5.5 | 6.0–7.5 |

Preferably, only dextrose is contained in chamber 1. In an embodiment, lactate is contained in chamber 1 along with dextrose.

The contents of the two chambers are mixed prior to infusion into the peritoneal cavity of the patient. The combined solution has the following composition:

| Dextrose (% w/v) | 0.5–4.0 |
|---|---|
| Polypeptides (% w/v) | 0.25–4.0 |
| Sodium (mEq/L) | 120.0–150.0 |
| Chloride (mEq/L) | 80.0–110.0 |
| Lactate (mEq/L) | 0.0–45.0 |
| Bicarbonate (mEq/L) | 0.0–45.0 |
| Calcium (mEq/L) | 0.0–4.0 |
| Magnesium (mEq/L) | 0.0–4.0 |
| pH | 6.0–7.4 |

As previously noted, pursuant to the present invention, synthetic peptides can also be utilized. Synthetic peptides provide better defined characteristics and contain less impurities compared to peptides. obtained by hydrolysis of proteins. The synthetic peptides should be approximately 2 to about 15 amino acids long. Preferably, the synthetic peptides comprise 4 to about 10 amino acids in length.

Pursuant to the present invention, the solution can be used for intraperitoneal drug delivery. Due to the size of peptides, one is able to keep the fluid in the peritoneum and thus avoid the problems of too rapid absorption experienced with saline and dextrose solutions.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A peritoneal dialysis solution comprising as osmotic agents:
   approximately 0.25 to about 4.0% (w/v) polypeptides having an average molecular weight of approximately 400 to about 900 daltons; and
   dextrose.

2. The peritoneal dialysis solution of claim 1 wherein the solution includes:
   approximately 120.00 to about 150.00 (mEq/L) of sodium; and
   approximately 80.0 to about 110.00 (mEq/L) of chloride.

3. The peritoneal dialysis solution of claim 2 wherein the solution includes:
   0 to about 45.00 (mEq/L) of lactate;
   0 to about 45.00 (mEq/L) of bicarbonate;
   0 to about 4.00 (mEq/L) of calcium; and
   0 to about 4.00 (mEq/L) of magnesium.

4. The peritoneal dialysis solution of claim 1 wherein the pH of the solution is approximately 6.0 to about 7.4.

5. The peritoneal dialysis solution of claim 1 wherein the polypeptides are synthetic peptides.

6. The peritoneal dialysis solution of claim 5 wherein the synthetic peptides are approximately 4 to about 10 amino acids long.

7. A peritoneal dialysis solution comprising as osmotic agents:
   approximately 0.25 to about 4.0% (w/v) polypeptides the molecular weight average of the polypeptides is approximately 400 to about 900 daltons; and
   appoximately 0.5% to about 4.0% (w/v) dextrose.

8. A peritoneal dialysis solution comprising a polypeptide mixture as an osmotically active agent in an osmotically effective amount, the polypeptide mixture consisting of:
   not more than approximately 0.10% of polypeptides having a molecular weight of greater than 1200;
   not more than approximately 25% of polypeptides having a molecular weight of less than 400; and
   the weight average of the polypeptide mixture being within the range of approximately 400 to about 900 daltons.

9. The peritoneal dialysis solution of claim 8 wherein the polypeptides include not less than 40% as essential amino acids.

10. The peritoneal dialysis solution of claim 8 wherein the solution provides less than approximately 5 ppm of total heavy metals.

11. The peritoneal dialysis solution of claim 8 wherein the solution provides less than approximately 500 ppb aluminum.

12. The peritoneal dialysis solution of claim 8 wherein the polypeptides in the solution provide less than approximately 50 mg/gm sodium.

13. The peritoneal dialysis solution of claim 8 wherein the polypeptides in the solution provide less than approximately 10 mg/gm chloride.

14. The peritoneal dialysis solution of claim 8 wherein the polypeptides in the solution provide less than approximately 0.2 mg/gm potassium.

15. The peritoneal dialysis solution of claim 8 wherein the polypeptides in the solution provide less than approximately 1 mg/gm magnesium.

16. The peritoneal dialysis solution of claim 8 wherein the polypeptides in the solution provide less than approximately 1 mg/gm calcium.

17. The peritoneal dialysis solution of claim 8 wherein the polypeptides in the solution provide less than approximately 1 mg/gm phosphorus.

18. The peritoneal dialysis solution of claim 8 wherein the polypeptides in the solution provide less than approximately 5 mg/gm of lactose.

19. The peritoneal dialysis solution of claim 8 including an additional osmotic agent.

20. The peritoneal dialysis solution of claim 8 wherein the solution includes as an osmotic agent dextrose.

21. The peritoneal dialysis solution of claim 8 wherein the polypeptides comprise approximately 0.25 to about 4.0% (w/v) of the solution.

22. The peritoneal dialysis solution of claim 8 wherein the pH of the solution is approximately 6.0 to about 7.4.

23. The peritoneal dialysis solution of claim 8 wherein the polypeptides are synthetic polypeptides.

24. The peritoneal dialysis solution of claim 23 wherein the synthetic peptides are approximately 2 to about 15 amino- acids long.

25. The peritoneal dialysis solution of claim 23 wherein the synthetic peptides are approximately 4 to about 10 amino acids long.

26. A peritoneal dialysis solution comprising as an osmotic agent synthetic polypeptides that are approximately 4to about 10 amino acids long and dextrose.

27. The peritoneal dialysis solution of claim 26 wherein the synthetic polypeptides comprise 0.25% to about 4.0% (w/v) of the solution.

28. The peritoneal dialysis solution of claim 26 wherein the synthetic polypeptides includes essential and non-essential amino acids.

29. The peritoneal dialysis solution of claim 26 wherein the dextrose comprise approximately 0.5 to about 4.0% (w/v) of the solution.

30. The peritoneal dialysis solution of claim 26 wherein the molecular weight average of the synthetic polypeptides is approximately 400 to about 900 daltons.

31. The peritoneal dialysis solution of claim 26 wherein the synthetic polypeptides comprise:

not more than approximately 0.10% of the polypeptides having a molecular weight of greater than 1200;

not more than approximately 25% of the polypeptides having a molecular weight of less than 400; and the weight average of polypeptides being within the range of approximately 400 to about 900 daltons.

32. A peritoneal dialysis solution comprising as one of at least two osmotic agents a polypeptide having the following amino acid composition:

| ASX | 10.3 |
|-----|------|
| GLX | 20.3 |
| SER | 4.5 |
| GLY | 2.3 |
| HIS | 2.4 |
| ARG | 2.3 |
| THR | 5.7 |
| ALA | 6.4 |
| PRO | 5.8 |
| TYR | 3.7 |
| VAL | 4.6 |
| MET | 2.3 |
| ILE | 4.7 |
| LEU | 11.7 |
| PHE | 3.4 |
| LYS | 9.7 | and including 50 to 150 mg of valine and 15 to 30 mg tryptophan per gm of polypeptide.

33. The peritoneal dialysis solution of claim 32 wherein the solution includes dextrose as an osmotic agent.

34. The peritoneal dialysis solution of claim 33 wherein the ratio of polypeptides to dextrose is 0.3 to 2 by weight.

* * * * *

UNITED STATES PATENT AND TRADEMARK OFFICE
CERTIFICATE OF CORRECTION

PATENT NO. : 6,380,163 B1
DATED : April 30, 2002
INVENTOR(S) : Leo Martis et al.

It is certified that error appears in the above-identified patent and that said Letters Patent is hereby corrected as shown below:

Column 1,
Line 24, delete ";".
Lines 24 and 34, delete ".".

Column 2,
Line 55, delete ".".

Column 4,
Line 36, delete ".".

Column 6,
Table 1, delete "Calcium mg/L" and insert -- Calcium (mEq/L) --.

Column 8,
Line 48, delete ",".

Column 9,
Line 18, insert -- Procedures (Example No. 2) --.
Line 45, delete ".".
Line 64, delete; "Groups5," and insert -- Groups 5, --.

Column 10,
Line 46, delete " 2Moderate" and insert -- 2 = Moderate --.

Column 11,
Line 35, delete ".".

UNITED STATES PATENT AND TRADEMARK OFFICE
CERTIFICATE OF CORRECTION

PATENT NO. : 6,380,163 B1
DATED : April 30, 2002
INVENTOR(S) : Leo Martis et al.

It is certified that error appears in the above-identified patent and that said Letters Patent is hereby corrected as shown below:

Column 12,
Line 34, insert -- and dextrose. -- after polypeptides.

Signed and Sealed this

Twenty-second Day of October, 2002

*Attest:*

*Attesting Officer*

JAMES E. ROGAN
*Director of the United States Patent and Trademark Office*